United States Patent [19]

D'Amico et al.

[11] 3,969,350

[45] July 13, 1976

[54] BASE CATALYSIS OF AZOLESULFENAMIDES AND SULFUR TO AMINODITHIOAZOLES

[75] Inventors: John J. D'Amico, Akron; Darrell D. Mullins, Norton, both of Ohio

[73] Assignee: Monsanto Company, St. Louis, Mo.

[22] Filed: July 1, 1974

[21] Appl. No.: 484,675

Related U.S. Application Data

[63] Continuation of Ser. No. 235,081, March 15, 1972, abandoned.

[52] U.S. Cl. .................. 260/247.1 H; 260/247.1 L; 260/293.54; 260/293.57; 260/293.58; 260/293.67; 260/293.68; 260/302 F; 260/302 H; 260/302 S; 260/306.5; 260/307 D; 260/309.2
[51] Int. Cl.² ........................................ C07D 277/78
[58] Field of Search .............. 260/247.1 H, 247.1 L, 260/306.5, 307 D, 302 H, 302 S, 302 F, 293.54, 293.57, 293.58, 293.67, 293.68, 309.2

[56] References Cited

UNITED STATES PATENTS

| | | | |
|---|---|---|---|
| 2,837,519 | 6/1958 | Hardman | 260/247.1 H |
| 3,001,993 | 9/1961 | Hendry et al. | 260/247.1 H |
| 3,133,920 | 5/1964 | Hardman | 260/247.1 H |
| 3,150,130 | 9/1964 | Hardman | 260/247.1 H |
| 3,595,871 | 7/1971 | Campbell | 260/247.1 H |

OTHER PUBLICATIONS

D'Amico et al., Rubber Chem. Technol., 41, pp. 704–720, (1968).

*Primary Examiner*—Lorraine A. Weinberger
*Assistant Examiner*—Michael Shippen

[57] ABSTRACT

The reaction of azolesulfenamides with sulfur to form aminodithioazoles is promoted by catalytic quantities of certain bases.

1 Claim, No Drawings

BASE CATALYSIS OF AZOLESULFENAMIDES AND SULFUR TO AMINODITHIOAZOLES

This application is a continuation of application Ser. No. 235,081 filed Mar. 15, 1972 now abandoned.

This invention relates to the preparation of aminodithioazoles from azolesulfenamides by reaction with sulfur. The aminodithioazoles and particularly 2-(morpholinodithio)-benzothiazole are valuable accelerators for vulcanization of natural and synthetic diene rubbers.

BACKGROUND OF THE INVENTION

Hardman U.S. Par. No. 2,837,519, June 3, 1958, described the reaction of 2-(morpholinothio)benzothiazole, sulfur and morpholine in ethanol to produce morpholinodithiobenzothiazole. Morpholine is referred to as a catalyst, but is used in molecular amount and attempts to reduce the dosage have proved unsuccessful. However, there has now been discovered materials which promote the reaction in catalytic amounts. The same product forms from reaction of 2,2'-dithiobis(benzothiazole) and N,N'-dithiobis(morpholine) which reaction is promoted by amines, Hardman U.S. Pat. No. 3,086,018, April 16, 1963, but substantial amounts are needed to achieve reasonable acceleration of the reaction as reported by D'Amico U.S. Pat. No. 3,489,754, Jan. 13, 1970, who found that the exchange reaction is catalyzed by certain alkali metal salts. This invention is concerned with improvements in the sulfur insertion reaction.

SUMMARY OF THE INVENTION

The general reaction according to the present invention is

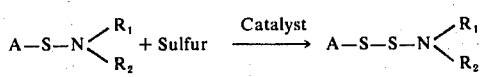

where

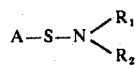

is an azolesulfenamide in which A is the radical of the azole,

is the amido radical and the catalyst may be generally described as the salt of a strong base and a weak acid, water being regarded as a weak acid in the scheme. For example, it has been discovered that the reaction is promoted by catalytic amounts of a base comprising an alkali metal salt of an acid having a dissociation constant equal to or less than that of $H_3PO_4$. The anion of the catalyst includes AS- where A has the same meaning as before, RS-, RO- where R is alkyl, aryl, aralkyl or cycloalkyl, $HS^-$, $HO^-$, $CO_3^{--}$, $PO_4^{---}$, $RC(O)O^-$, $RC(S)S^-$, and

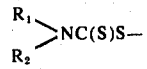

where R and

have the same meaning as before. Preferred is a thio anion of the general formula SX capable of bearing a formal charge on the sulfur.

The dissociation constant of the first hydrogen of $H_3PO_4$ is $1.6 \times 10^{-2}$ and the experimental evidence indicates that alkali metal salts of acids having dissociation constants equal to or less than $1.6 \times 10^{-2}$ function as catalysts for the insertion of sulfur into azolesulfenamides but it will be appreciated that a sulfur extraction agent like KCN should not be selected. The salt may be formed in situ by adding both a suitable alkali metal salt forming reagent and the selected acid to the reaction mixture but alkali metal salt forming reagents are not necessarily equivalent probably due to different solubilities in the reaction medium and it is generally desirable to select a reagent soluble in the medium. Moreover, it whould be borne in mind that sulfenamides react rapidly with certain thioacids. In fact, reaction with mercaptobenzothiazole constitutes a method for quantitative analysis of sulfenamides, Behforouz and Kerwood, Journal of Organic Chemistry 34, p. 55, Jan. 1969. Accordingly, it is highly desirable to add the salt forming reagent first, followed by the thioacid. In most instances, a number of moles of catalyst, calculated on the basis of monobasic equivalency, which is 5–20% of the number of moles of thiazolesulfenamide to be reacted, gives satisfactory results but higher or lower amounts may be although no advantage is observed with higher amounts and amounts which exceed say 50% of the number of moles of thiazolesulfenamide are not regarded as catalytic amounts for the purposes of this invention.

The reaction of sulfur and azolesulfenamides has been recognized to be a general one of the catalysts of the present invention promote the general reaction. The azole residue A in the sulfenamide reactant is independent of A in the catalyst but in either case A may be, for example, aryleneazolyl represented by benzothiazolyl, naphthothiazoyl, benzoxazolyl, benzimidazolyl, or substituted aryleneazole wherein the substituents are chlorine, bromine, lower alkyl of 1–5 carbon atoms, lower alkoxy or nitro. Also, A may be thiazolyl or substituted thiazolyl where the substituents may be lower alkyl, lower acyl or lower alkoxy carbonyl or A may be tetrahydrobenzothiazolyl. The radicals designated as $R_1$ and $R_2$ are selected from a group consisting of lower alkyl, benzyl, alicyclic of 5–8 carbon atoms or together with the nitrogen form a heterocycle, for example, morpholino, dimethylmorpholino, 3-azabicyclo[3.2.2]non-3-yl or polymethylenimino comprising 4–8 methylene groups, one or more of which may be substituted by lower alkyl.

Representative examples of A-S-M catalysts where A has the same meaning as before and M is alkali metal comprise the potassium or sodium salts of mercaptothiazole, mercaptobenzothiazole, mercaptobenzoxazole or mercaptobenzimidazole. In some instance, amine addition salts of the formula

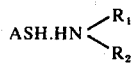

the filtered product is sucked dry and washed with one liter of water before air drying in order to remove excess sodium phosphate which has very low solubility in isopropanol.

Table I

| Acid | Moles | Base | Moles | Yield, % |
| --- | --- | --- | --- | --- |
| 2-Mercaptobenzothiazole | 0.01 | $K_2CO_3$ | 0.005 | 97.9 |
| 2-Mercaptobenzothiazole | 0.01 | $K_2CO_3$ | 0.01 | 97.5 |
| 2-Mercaptobenzothiazole | 0.01 | $Na_3PO_4.12H_2O$ | 0.0033 | 91.9 |
| 2-Mercaptobenzothiazole | 0.01 | $Na_3PO_4.12H_2O$ | 0.01 | 91.6 |
| 2-Mercaptobenzimidazole | 0.01 | NaOH | 0.01 | 91.6 |
| 2-Mercaptobenzoxazole | 0.01 | NaOH | 0.01 | 92.8 |
| 2-Mercaptobenzothiazole | 0.01 | $KO(O)CCH_3$ | 0.01 | 98.0 |
| 2-Mercaptobenzothiazole | 0.01 | $NaO(O)CCH_3$ | 0.01 | 94.5 |
| 2-Mercaptobenzothiazole | 0.01 | KSCN | 0.01 | 95.1 | especially the morpholine and piperidine salts of the aforesaid mercaptoazoles exert significant catalytic activity but of a lower order than alkali metal salts. Representative examples of RSM catalysts are sodium thiophenate, potassium thiophenate and potassium butyl mercaptide. The radicals designated R, when aryl, may be substituted by chlorine, bromine, lower alkyl, lower alkoxy or nitro. Examples of inorganic catalysts are sodium hydroxide, potassium hydroxide, trisodium phosphate and sodium hydrosulfide.

DESCRIPTION OF PREFERRED EMBODIMENTS

EXAMPLE 1 — 2-(Morpholinodithio)benzothiazole

There is charged to a glass or glass-lined reactor 25.2 grams (0.1 mole) of 2-(morpholinothio)benzothiazole, 3.2 grams (0.1 mole) of sulfur, and 150 ml. of essentially anhydrous isopropyl alcohol (0.4% by weight water). The catalyst, the sodium salt of mercaptobenzothiazole, is used in amount of 0.01 mole and is formed in situ by adding 0.01 mole of solid sodium hydroxide and then 0.01 mole of 2-mercaptobenzothiazole (MBT) to the reaction mixture. The reaction mixture is then stirred and heated at refluxing temperature (about 82–83°C) for 2 hours although it is found that the reaction is essentially complete in one hour. A clear solution usually forms in from 15 to 75 minutes. The reaction mixture is cooled to 30°C. during which cooling a precipitate usually begins to form in the range of 67–74°C. Stirring and cooling is continued to 0°C. and the mixture is held at 0-10°C. for about 30 minutes after which it is filtered and the solids air dried at 25–30°C. There is obtained a yield of 94.4–95% of 2-(morpholinodithio)benzothiazole, m.p. 132°–136°C. Calculated for $C_{11}H_{12}N_2OS_3$: N 9.85%, S 33.8%; Found: N 9.75%, S 34.04%. The results are essentially the same with 0.05 mole of catalyst but no improvement is observed with increasing catalyst concentration.

In the foregoing procedure 2-mercaptobenzothiazole is replaced by 2-mercaptobenzimidazole and 2-mercaptobenzoxazole, respectively, or sodium hydroxide is replaced by alkali metal carbonate, phosphate, acetate and thiocyanate, respectively, with results as summarized in Table I below. In most cases, the results are from 0.1 mole reactions of 2-(morpholinothio)benzothiazole and sulfur but in all cases the moles of acid and base are calculated on the basis of 0.1 mole reactions. It will be noted that with polybasic salts the results are comparable whether the proportion of base is equivalent to the mercaptobenzothiazole or is added in equal molecular proportion. In the sodium phosphate runs Reducing the concentration of 2-mercaptobenzothiazole and potassium acetate by 50% significantly lowers the yield but it is still high (93.5%). A similar reduction of 2-mercaptobenzothiazole and sodium acetate has a more dramatic effect and the yield drops to 86.4%.

Results with other catalysts which promote the reaction in amounts of 10 mole percent are summarized in Table II. The reaction procedure is the same as described in Example 1. With potassium hydroxide or sodium hydroxide a completely clear solution is not usually observed during the refluxing period, but in other instances the appearance of the reaction mixture is essentially the same as when using sodium salt of mercaptobenzothiazole as the catalyst. In each case the amount of catalyst is 0.01 mole per 0.1 mole of reactants.

Table II

| Catalyst | Yield, % |
| --- | --- |
| Sodium hydroxide | 91.3 |
| Potassium hydroxide | 93.7 |
| Sodium hydrosulfide | 90.5 |
| Sodium dimethyldithiocarbamate | 84.5 |
| Sodium isopropyl xanthate | 90.0 |
| Sodium thiophenate | 84.5 |
| Sodium ethylate | 88.7 |
| Sodium phosphate ($Na_3PO_4.12H_2O$) | 88.7 |
| Potassium thiocyanate | 83.1 |
| Potassium acetate | 82.0 |

Omitting the catalyst and refluxing the reactants for 48 hours yields none of the desired product. The product obtained m.p. 78°–80°C. after recrystallization from isopropyl alcohol melts at 132°–134°C. but contains 7.86% nitrogen and 43.8% sulfur whereas the calculated value for $C_{11}H_{12}N_2OS_3$ are 9.85% nitrogen and 33.82% sulfur. The addition of 0.01 mole of morpholine as the catalyst is similarly ineffective giving a product m.p. 80°–82°C. which after two recrystallizations melts at 84°–85°C. and contains 10.22% nitrogen and 30.18% sulfur. However, using 0.1 mole of morpholine results in 88% yield of the desired product.

The effectiveness of catalytic amounts of bases contrasts with the preparation of aminodithioazoles from 2,2'-dithiobisthiazoles as described by Hardman U.S. Pat. No. 3,150,130 Sept. 22, 1964. It has been known since 1937 that amines react with 2,2'-dithiobis(benzothiazole), Harman U.S. Pat. No. 2,100,692 Nov. 30, 1937, but in the presence of sulfur and morpholine, Hardman, supra, observed no formation of 2-(morpholinodithio)-benzothiazole but said product formed upon addition of molecular quantities of certain bases.

The process advantageously follows neat preparation of the intermediate by the transamidation method of Campbell and D'Amico U.S. Pat. No. 3,595,871 July 27, 1971. Solvent, sulfur and catalyst are added to the product of said method usually in the same reaction vessel in which it is prepared and the aforedescribed sulfur insertion reaction effected. A typical procedure illustrative of the process in combination with transamidation is as follows.

A stirred slurry containing 48.4 g (0.2 mole) of N-tertiary-butyl-2-benzothiazolesulfenamide and 22 g (0.25 mole) of morpholine (25% excess) is heated at 90°–95°C. at 760 mm. for 1 hour. A solution forms at 65°C. During the heating period tert-butylamine is collected. Vacuum is applied and the stirred solution is heated at 90°–95°C. at 10–15 mm. for 15 minutes and at 90°–95°C. at 1–5 mm. for 15 minutes in order to remove all of the tert-butylamine and excess morpholine. After releasing the vacuum, 300 ml. of isopropyl alcohol, 6.4 g (0.2 mole) of sulfur, 1.38 g (0.01 mole) of $K_2CO_3$ (5%) and 3.4 g. (0.02 mole) of MBT (10%) are added to the stirred molten 2-morpholinothiobenzothiazole. The stirred slurry is heated at reflux (82°–83°C.) for 2 hours. After 27 minutes at these temperatures a solution results. The stirred solution is allowed to cool at 30°C. (thick ppt. forms at 69°C). The stirred slurry is cooled to 0°C, held at 0°–10°C. for 30 minutes, filtered and air-dried at 25°–30°C. The product, m.p. 133°–4°C, is obtained in 98.190 overall yield bases on N-tertiary-butyl-2-benzothiazolesulfenamide. Six grams of the product recrystallized from 100 ml. of $(CH_3)_2CHOH$ furnish 5.3 g, m.p. 136°–7°C. Calculated for $C_{11}H_{12}N_2OS_3$: N 9.85%, S 33.83%; Found: N 9.83%, S 33.99%.

EXAMPLE 2 —
2-(1-hexamethyleniminedithio)benzothiazole

A stirred slurry containing 52.9g (0.2 mole) of 2-(1-hexamethyleniminothio)benzothiazole, 6.4 g (0.2 mole) of S, 3.4 g (0.02 mole) of MBT, 1.38 g (0.01 mole) of $K_2CO_3$ in 100 ml. of isopropyl alcohol is heated at reflux (82°–83°C) for 2 hours. A solution results after 1 hour at these temperatures. The stirred solution is allowed to cool to 30°C. (thick ppt. forms at 47°C). The stirred slurry is cooled to 0°C, held at 0°–10°C. for 30 minutes, filtered and air-dried at 25°–30°C. 2-(1-Hexamethyleniminedithio)benzothiazole, also named 2-(hexahydro-1H-azepin-1-yldithio)-benzothiazole, m.p. 65°–7°C, is obtained in 83.5% yield. After recrystallization from isopropyl alcohol it melts at 70°–71°C. Calculated for $C_{13}H_{16}N_2S_3$: N 9.45%, S 32.45%; Found: N 9.35%, S 32.30%.

Substituting 0.2 mole of 2-(piperidinothio)benzothiazole and 0.2 mole of 3-(benzothiazol-2-ylthio)azabicyclo-[3.2.2]nonane respectively in the foregoing procedure gives the corresponding dithio compounds in the indicated yields.

The aminodithioazole produced will not correspond to azolesulfenamide reacted if transamidation and sulfur insertion are both carried out which reactions may be effected simultaneously. Preparing 2-(morpholinodithio)thiazoles by reacting morpholine and sulfur with a thiazolesulfenamide in which the nitrogen substituents are hydrogen, cyclohexyl or lower alkyl is described by Hardman U.S. Pat. No. 3,133,920 May 19, 1964. Catalytic quantities of sulfur promote transamidation and molecular quantities promote the simultaneous reactions of transamidation and sulfur insertion. Substantial yields of animodithiothiazole are obtained so that the effect of basic catalysts may be obscured. Nevertheless, unmistakable improvement is observed by the further addition of properly selected basic catalyst as hereinafter demonstrated although the order of catalyst effectiveness does not necessarily correspond to that for sulfur insertion alone.

EXAMPLE 3 — Simultaneous Reactions

There is charged to a glass or glass-lined reactor 96.8 grams (0.40 mole) of N-tertiary-butyl-2-benzothiazolesulfenamide. 12.8 grams (0.40 mole) of sulfur, 35.2 grams (0.40 mole) of morpholine, 600 ml. of isopropanol and 0.04 mole of sodium carbonate. There is then added 0.04 mole of MBT. The reaction mixture is stirred and heated at refluxing temperature (82°–83°C) for 2 hours. The stirred solution is allowed to cool to about 30°C at which temperature it is a slurry of precipitated solids in the isopropanol. The stirred slurry is cooled to 0°C, held at 0°–10°C. for 30 minutes, filtered and the filtered solids air-dried at 25°–30°C. There is obtained a yield of 99.8% of 2-(morpholinodithio)benzothiazole, m.p. 134°–135°C. Calculated for $C_{11}H_{12}H_2OS_3$: N 9.85%, S 33.82%; Found: N 9.83%, S 33.22%.

In the absence of sodium salt of mercaptobenzothiazole the yield is about 16% lower. The base used with the mercaptobenzothiazole affects the results but the catalytic effect is discernible in Table III below from comparison of yields with the yield from reaction without addition of either base or mercaptobenzothiazole. The procedure is the same as in Example 3 and the proportion of acid and base are the same, namely 0.04 mole of each per 0.4 mole of N-tertiary-butyl-2-benzothiazolesulfenamide. Doubling the amount of KOH and MBT give the same yield as does reducing the sodium phosphate to one-third of the indicated amount.

Table III

| Base | Catalyst Acid | Yield, % | |
|---|---|---|---|
| None | None | 83.3 | Avg. |
| NaOH | MBT | 86.3 | |
| KOH | MBT | 86.3 | |
| Sodium acetate | MBT | 97.5 | Avg. |
| Potassium acetate | MBT | 95 | Avg. |
| $Na_3CO_3$ | MBT | 99.8 | |
| $K_2CO_3$ | MBT | 85.0 | Avg. |
| NaSH | MBT | 94.4 | |
| $(CH_3)_2NC(S)SNa.2H_2O$ | MBT | 90.3 | |

| Product | Yield % | M.P. | Analysis |
|---|---|---|---|
| 2-(Piperidinodithio)-benzothiazole | 96.1 | 86–87 | Calcd. for $C_{12}H_{14}N_2S_3$: N 9.92%, S 34.06%; Found: N 9.86%, S 33.83% |
| 3-(Benzothiazol-2-yl-dithio)-3-azabicyclo-[3.2.2]nonane | 97.0 | 117–119 | Calcd. for $C_{15}H_{18}N_2S_3$: N 8.69%, S 29.83%; Found: N 8.78%, S 29.85% |

Table III-continued

| Catalyst | | |
|---|---|---|
| Base | Acid | Yield, % |
| C₂H₅ONa | MBT | 87.2 |
| KSCN | MBT | 90.5 |
| Na₃PO₄.12H₂O | MBT | 88.2 |

In general, any effect of the base component along is obscured by the presence of sulfur in the simultaneous reactions.

The reaction is preferably carried out in a solvent inert to the reactants which is essentially anhydrous. The presence of significant amounts of water is isopropanol reaction medium at refluxing temperature has been observed to lower the yield but the effect is less pronounced at lower reaction temperatures. Nevertheless, it is preferred that the water content of the reaction mixture be kept at 1% or lower. Typical suitable solvents comprise methanol, ethanol, isopropanol, butanol, benzene, chlorobenzene, tolune, xylene and chloroform.

Sutstituting an equivalent molecular proportion of the appropriate 2-(morpholinothio)azole in the procedure of Example 1 yields the following products: 2-(morpholinodithio)-5-chlorobenzothiazole, 2-(morpholinodithio)-6-ethoxybenzothiazole, 2-(morpholinodithio)-6-nitrobenzothiazole, 2-(morpholinodithio)-benzoxazole, 2-(morpholinodithio)-benzimidazole, 2-(morpholinodithio)-4-methylthiazole, 2-(morpholinodithio)-5-acetyl-4-methylthiazole, 2-(morpholinodithio)-5-ethoxycarbonyl-4-methylthiazole. All of the aforesaid products are solids except 2-(morpholinodithio)-4-methylthiazole, which is a liquid under ordinary conditions.

Substituting equivalent molecular proportions of the appropriate benzothiazolesulfenamide sulfur and catalyst in the procedure of Example 1 yields the following products:

2-(2,6-dimethylmorpholinodithio)benzothiazole, a very viscous amber liquid, 2,2'-(1,4-piperazinediylbisdithio)bis benzothiazole, m.p. 172°–173°C, 2-(1,2,3,4-tetrahydro-2-isoquinolinyldithio)benzothiazole, a very viscous amber liquid, 2-(1,2,3,4,4a,5,6,7,8,8a-decahydro--de 1-quinolinyldithio)-benzothiazole, a very viscous amber liquid, 2-(1-indolinyldithio)benzothiazole, m.p. 114°–115°C, 2-[4-(3-phenylpropyl)piperidinodithio]benzothiazole, m.p. 79°–80°C, Ethyl 4-(2-benzothiazolyldithio)piperazine carboxylate, a very viscous amber liquid, 2-(4-benzyl-1-piperazinyldithio)benzothiazole, m.p. 104°–105°C, and 2-(1-pyrrolidinyldithio)benzothiazole, m.p. 63°–64°C.

Although the invention has been illustrated by typical examples, it is not limited thereto. Changes and modifications of the examples of the invention herein chosen for purposes of disclosure can be made which do not constitute departure from the spirit and scope of the invention.

The embodiments of the invention in which an exclusive property or privelege is claimed are defined as follows:

1. The method of preparing an aminodithioazole which comprises reacting sulfur and azolesulfenamide of the formula

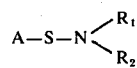

in which A is selected from the class consisting of
a. aryleneazole selected from the group consisting of benzothiazolyl, naphthothiazolyl, benzoxazolyl and benzimidazolyl,
b. substituted said aryleneazole in which the substituents are chlorine, bromine, lower alkyl, lower alkoxy or nitro,
c. thiazolyl,
d. substituted thiazolyl in which the substituents are lower alkyl, lower acyl or lower alkoxy carbonyl and
e. tetrahydrobenzothiazolyl, R₁ and R₂ are selected from the group consisting of lower alkyl, benzyl, alicyclic of 5 to 8 carbon atoms, and together with the nitrogen R₁ and R₂ form a heterocycle selected from the group consisting of morpholino, dimethylmorpholino, 3-azabicyclo(3.2.2)non-3-yl and polymethyleneimino of 4 to 8 methylenes one or more of which are optionally substituted by lower alkyl in the presence of about 5–20% of the number of moles of azolesulfenamide of a catalyst selected from the group consisting of alkali metal hydrosulfide, alkali metal hydroxide, alkali metal salt of mercaptobenzothiazole, alkali metal salt of mercaptobenzimidazole, alkali metal salt of mercaptobenzoxazole, alkali metal salt of di(lower alkyl)dithiocarbamic acid, alkali metal salt of lower alkyl xanthic acid, alkali metal salt of thiophenol, alkali metal lower alcoholate, alkali metal thiocyanate and alkali metal phosphate.

2. The method of claim 1 in which the azolesulfenamide is morpholinothiobenzothiazole.

3. The method of claim 2 in which the reaction is effected in a lower aliphatic alcohol and the catalyst is an alkali metal salt of mercaptobenzothiazole.

4. The method of claim 1 in which the anion of the catalyst is a thioanion.

5. The method of claim 1 in which the catalyst is formed in situ from alkali metal hydroxide and mercaptobenzothiazole.

6. The method of claim 2 in which the alkali metal is potassium.

7. In the method of preparing an aminodithioazole by reacting sulfur, amine, the radical of which replaces the amido radical of the azolensulfenamide, and azolesulfenamide of the formula

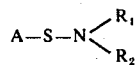

in which A is selected from the class consisting of
a. aryleneazole selected from the group consisting of benzothiazolyl, naphthothiazolyl, benzoxazolyl and benzimidazolyl,
b. substituted said aryleneazole in which the substituents are chlorine, bromine, lower alkyl, lower alkoxy or nitro;
c. thiazolyl, d. substituted thiazolyl in which the substituents are lower alkyl, lower acyl or lower alkoxy carbonyl and e. tetrahydrobenzothiazolyl, $R_1$ and $R_2$ are selected from the group consisting of lower alkyl, benzyl, alicyclic of 5 to 8 carbon atoms, and together with the nitrogen $R_1$ and $R_2$ form a heterocycle selected from the group consisting of morpholino, dimethylmorpholino, 3-azabicyclo(3.2.2)non-3-yl and polymethyleneimino of 4 to 8 methylenes one or more of which are optionally substituted by lower alkyl, the improvement which comprises carrying out the reaction of the presence of about 5–20% of the number of moles of azolesulfenamide of a catalyst selected from the group consisting of alkali metal hydrosulfide, alkali metal hydroxide, alkali metal salt of mercaptobenzothiazole, alkali metal salt of mercaptobenzimidazole, alkali salt saot of mercaptobenzoxazole, alkali metal salt of di(lower alkyl)dithiocarbamic acid, alkali metal salt of lower alkyl xanthic acid, alkali metal salt of thiophenol, alkali metal lower alcoholate, alkali metal thiocyanate and alkali metal phosphate.

8. The method of claim 7 in which the catalyst is alkali metal salt of mercaptobenzothiazole.

9. The method of claim 7 in which the sulfenamide is N-tertiary-butyl-2-benzothiazolesulfenamide and the amine is morpholine.

* * * * *